United States Patent [19]

Seger

[11] 3,996,509
[45] Dec. 7, 1976

[54] CONDUCTIVITY DIP CELL
[75] Inventor: Edward J. Seger, Apollo, Pa.
[73] Assignee: Aluminum Company of America, Pittsburgh, Pa.
[22] Filed: Aug. 12, 1975
[21] Appl. No.: 604,005
[52] U.S. Cl. .......................... 324/30 B; 324/30 R
[51] Int. Cl.² ...................................... G01N 27/42
[58] Field of Search ....................... 324/30 R, 30 B

[56] References Cited
UNITED STATES PATENTS

| 3,219,556 | 11/1965 | Arthur et al. | 324/30 R |
| 3,505,196 | 4/1970 | Dahms | 324/30 R |
| 3,934,193 | 1/1976 | Hall | 324/30 B |

Primary Examiner—Robert Segal
Assistant Examiner—Michael J. Tokar
Attorney, Agent, or Firm—John P. Taylor

[57] ABSTRACT

A conductivity dip cell construction is provided which permits liquids to enter the dip cell electrode while inhibiting the passage of gases such as bubbles, foam, or the like, into the cell. The cell is provided with means to purge the liquid from the cell to permit subsequent entrance of a fresh aliquot of liquid for subsequent conductivity measurement.

4 Claims, 4 Drawing Figures

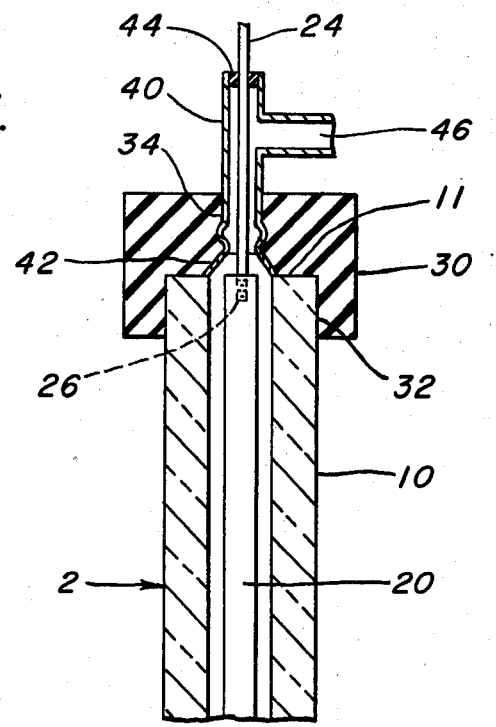
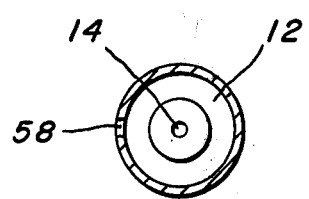
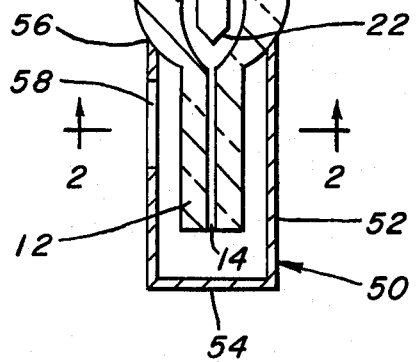

CONDUCTIVITY DIP CELL

BACKGROUND OF THE INVENTION

This invention relates to dip cells for the measurement of conductivity of liquid. More particularly, it relates to improved construction of dip cells.

In the measurement of conductivity of a liquid, a conductivity dip cell is commonly used which comprises an electrode surrounded by a non-conductive envelope having a capillary opening therein through which the liquid may pass to come in contact with the electrode. The capillary opening is of a given length thereby providing a resistance path which will vary with the conductivity of the liquid. The remainder of the bath as well as an electrode immersed in the bath, form the opposite electrode of the dip cell because the overall resistivity of the bath is very low compared to the high resistance path through the capillary.

In making such measurements, however, error can be introduced if the gases, foam, or other non-completely liquid materials enter the capillary passageway thus changing the resistance in the passageway. Furthermore, whether the material in the capillary is liquid or some undesirable gaseous-liquid mixture, it is sometimes difficult to remove the material from the capillary to permit a subsequent fresh reading of liquid from the bath.

It is therefore an object of this invention to provide means for inhibiting the entry of such gaseous materials into the capillary tube.

It is a further object of the invention to provide means for purging the capillary passageway of a conductivity dip cell of gas or liquids to permit subsequent entry of fresh liquid into the dip cell for subsequent measurement.

SUMMARY OF THE INVENTION

In accordance with the invention, an improved conductivity dip cell for measuring the electrical conductivity of a liquid is provided comprising a hollow, non-conductive housing; an electrical conductor within said housing; terminal means externally mounted on said housing an in electrical communication with said conductor; a capillary passageway through the housing to the conductor; means for inhibiting the passage of non-liquids into said capillary passageway; and means for purging said housing of liquids comprising a gas inlet whereby a gas admitted into the housing forces out liquids from inside the housing and from the capillary passageway to permit a new liquid sample to be subsequently introduced into the capillary passageway and measured.

BRIEF DESCRIPTION OF THE DRAWINGS

FIG. 1 is a vertical cross sectional view of the preferred construction of the dip cell of the invention.

FIG. 2 is a sectional view of the dip cell of FIG. 1 taken along lines 2—2.

DESCRIPTION OF THE INVENTION

Figure 3:
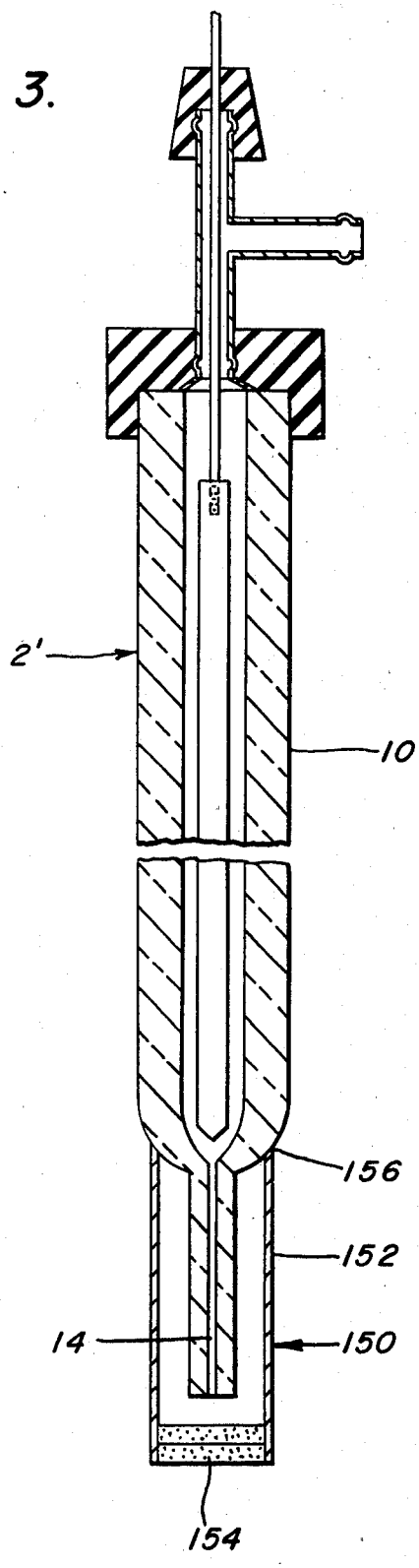
FIG. 3 is a vertical cross section of an alternate construction of the dip cell.

Referring now to FIG. 1, a dip cell constructed in accordance with the invention is generally indicated at 2. Dip cell 2 comprises an outer non-conductive hollow housing 10, which in the illustrated embodiment is tubular, and an inner electrode 20. Housing 10 terminates at one end in a capillary tube 12 having a capillary passageway 14 therein. Inner electrode 20 terminates at an end point 22 just above capillary passageway 14. Liquids from the bath to be measured for conductivity pass through the capillary opening 14 to come in electrical contact with end 22 of electrode 20.

The opposite end of hollow housing 10 is fitted with a cap 30 having a bore 32 which snugly receives end 11 of housing 10. Cap 30 also has a smaller counter bore 34 passing concentrically aligned with bore 32 and passing through the end of cap 30. A smaller hollow tube 40 passes through bore 34 and may be sealed to housing 10 at 42. Tube 40 carries a terminal portion 24 of electrode 20 which is fastened to electrode 20 at 26. Terminal 24 passes through the end of tube 40 to which it is joined by a seal 44 which also provides a mechanical support for electrode 20. A side tube or T-portion 46 is provided for communication with a source of gas as will be described below.

Turning now to FIGS. 1 and 2, a dip cell 2 is provided, in accordance with the invention, with a protective cap-like member 50 which generally surrounds the capillary tube 12 adjacent the bottom end of dip cell 2. Cap 50, in the illustrated embodiment, is generally cylindrical having a side wall 52 and a bottom wall 54. Side wall 52 is in turn sealed to housing 10 at 56. Still referring to FIGS. 1 and 2, it can be seen that cap 50 is provided with a slot 58 in side wall 52 which extends part way down the side wall but, as better seen in FIG. 1, terminates above the end of capillary tube 12.

Slot 58 permits liquids to enter into cap 50 and to pass from there into the interior of housing 10 via capillary passageway 14. However, because bubbles or froth or other gaseous elements inside a liquid tend to rise, the passage of such gaseous materials into capillary passageway 14 is severely inhibited by the protective cap 50 when dip cell 2 is mounted in a vertical position.

Turning now to FIG. 3, an alternate construction is shown wherein dip cell 2' includes a protective cap 150 having a tubular side wall 152 joined to housing 10 at 156. Cap 150 is fitted with an end plug 154 which comprises a porous frit material such as quartz or the like which in the illustrated embodiment is about 2 to 2½ millimeters thick. This frit has a porosity preselected to permit the passage of liquid therethrough to capillary passageway 14 while inhibiting or blocking the passage of gas or bubbles or froth, or the like, therethrough. Such porosity may range from about 100 to 300 microns depending upon the particular bath constituents. While the fritted material has been illustrated as an end plug, it should be recognized that any portion or all of cap 150 may comprise such fritted material.

Figure 4:
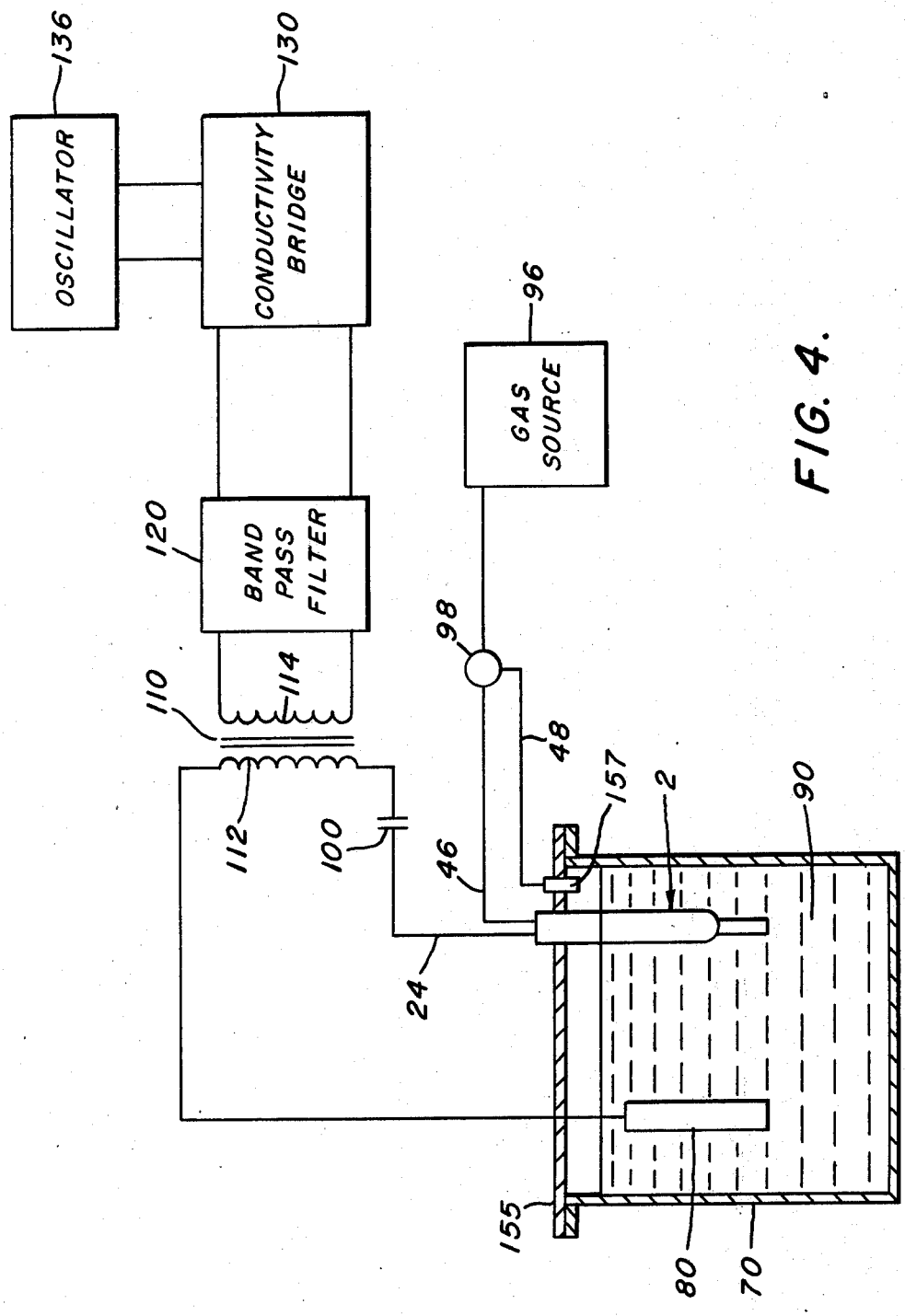
FIG. 4 is a schematic illustration showing operation of the dip cell in a bath.

Turning now to FIG. 4, a vessel 70 is shown containing a conventional electrode 80 such as the anode of a reduction cell for the production of aluminum. Vessel 70 contains a liquid 90 therein which may, for example, comprise a molten bath of halogen salts used as the electrolyte in an aluminum reduction cell. Dip cell 2 is immersed in liquid 90 in vessel 70 and connected via terminal 24 to a capacitor 100 to an isolation transformer 110 having the other leg of its primary winding 112 connected to anode 80. Capacitor 100 provides a blocking capacitor to prevent the passage of dc current therethrough. This may comprise, for example, a 600 microfarad capacitor. Isolation transformer 110 provides further protection against accidental dc coupling from the bath to the conductivity measurement equipment.

Secondary winding 114 on isolation transformer 110 is connected to a band pass filter 120 which is preselected to pass the particular ac frequency used to measure the conductivity. The signal is then passed from filter 120 to conductivity bridge 130 which is powered by an oscillator 136 preset to the particular ac frequency used for the measurement. In operation then, the dip cell is inserted into liquid 90 and a measurement taken. It should be noted that the exact position of the dip cell electrode 2 with respect to anode 80 is not important since the resistive path from anode 80 through liquid 90 to the entrance of the capillary passageway 14 is very low compared to the high resistance path along the length of passageway 14. Since passageway 14 is of a fixed length, this resistance (for a given liquid of given conductivity) is a constant. Thus, if the dip cell is inadvertently moved in the bath, the calibration is not materially affected.

In accordance with the invention, after a measurement is made, liquid 90 within dip cell 2 may be purged therefrom by passing gas from a gas source 96 into the interior of the cell via tube 46. This can be done conveniently by the use of a valve 98 which turns on the gas when the purging is desired. The gas is then turned off and a new sample of liquid allowed to enter passageway 14. In this manner, as the concentration of the bath changes with time, the liquid in passageway 14 will be truly representative of the make-up of the bath at the time of measurement. If vessel 70 is a closed vessel (using top 155) with varying pressures, valve 98 can be a three-way valve connected to dip cell 2 and a port 157 respectively via lines 46 and 48. This permits equalization of the pressure inside vessel 70 and dip cell 2 after each purge.

What is claimed is:

1. An improved conductivity dip cell for measuring the electrical conductivity of a liquid which comprises:
    a. a hollow non-conductive housing;
    b. an electrical conductor within said housing;
    c. terminal means externally mounted on said housing and in electrical communication with said conductor;
    d. a capillary passageway through said housing to said conductor; and
    e. a cap-like member having an opening therein, said member being carried by said housing and surrounding said capillary passageway to inhibit the passage of non-liquids into said passageway.

2. The dip cell of claim 1 wherein the opening in said cap-like member is spaced from said capillary and positioned with respect thereto to inhibit passage of non-liquids through said opening and into said capillary passageway when the dip cell is operated in a substantially vertical position.

3. An improved conductivity dip cell for measuring the electrical conductivity of a liquid which comprises:
    a. a hollow non-conductive housing;
    b. an electrical conductor within said housing;
    c. terminal means externally mounted on said housing and in electrical communication with said conductor;
    d. a capillary passageway through said housing to said conductor;
    e. means for inhibiting the passage of non-liquids into said capillary passageway; and
    f. means for purging said housing of liquids comprising a gas inlet whereby gas admitted into said housing forces out liquids from inside the housing and from the capillary passageway to permit a new liquid sample to be subsequently measured.

4. The conductivity dip cell of claim 1 wherein means are provided for purging said housing of liquids comprising a gas inlet whereby gas admitted into said housing forces out liquids from inside the housing and from the capillary passageway to permit a new liquid sample to be subsequently measured.

* * * * *